United States Patent [19]

Wright

[11] Patent Number: 5,547,677
[45] Date of Patent: Aug. 20, 1996

[54] ANTIMICROBIAL OIL-IN-WATER EMULSIONS

[75] Inventor: D. Craig Wright, Gaithersburg, Md.

[73] Assignee: Novavax, Inc., Rockville, Md.

[21] Appl. No.: 246,868

[22] Filed: May 20, 1994

[51] Int. Cl.$^6$ .............................. A61K 7/40; A61K 9/107
[52] U.S. Cl. ........................................................ 424/401
[58] Field of Search .................................................. 424/401

[56] References Cited

U.S. PATENT DOCUMENTS

| | | | |
|---|---|---|---|
| 4,006,218 | 2/1977 | Sipos | 424/54 |
| 4,091,090 | 5/1978 | Sipos | 424/45 |
| 4,147,663 | 4/1979 | Rutledge | 252/428 |
| 4,197,318 | 4/1980 | Sipos | 424/326 |
| 4,321,257 | 3/1982 | Sipos | 424/80 |
| 4,323,551 | 4/1982 | Parran, Jr. | 424/54 |
| 4,383,937 | 5/1983 | Williams | 252/389 R |
| 4,474,748 | 10/1984 | Sipos | 424/40 |
| 4,636,525 | 1/1987 | Ochiai et al. | 514/786 |
| 4,902,720 | 2/1990 | Baldone | 514/642 |
| 5,039,688 | 8/1991 | Lewis | 514/538 |
| 5,104,736 | 4/1992 | Walloch | 428/402.2 |
| 5,176,901 | 1/1993 | Gallopo et al. | 424/54 |
| 5,292,529 | 3/1994 | Gregory et al. | 424/59 |
| 5,300,305 | 4/1994 | Stapler et al. | 424/490 |
| 5,328,455 | 1/1995 | Kealey et al. | 424/73 |
| 5,362,494 | 11/1994 | Zysman et al. | 424/401 |

OTHER PUBLICATIONS

Pinnaduwage et al., (1989) "Use Of A Quaternary Ammonium Detergent In Liposome Mediated DNA Transfection of Mouse L–Cells", *Biochimica et Biophysica Acta*, vol. 985, pp. 33–37.

*McCutcheon's Detergents & Emulsifers 1971 Annual,* (New Jersey: Allured Publishing Company 1971), pp. 49, 86.

*Remington's Pharmaceutical Sciences* (1985), 17th Edition: pp. 317–318, 328.

*Primary Examiner*—Marianne M. Cintins
*Assistant Examiner*—Keith MacMillan

[57] ABSTRACT

An antimicrobial lipid-containing oil-in-water emulsion comprising an agent selected from the group consisting of glycerol monooleate, glycerol trioleate, glycerol monolaurate, and glycerol dilaurate as the primary lipid and a cationic halogen-containing compound having a $C_{12}$–$C_{16}$ chain as a positive charge producing agent is disclosed. The antimicrobial emulsion can be used in the form of a pharmaceutical preparation to inhibit the growth of a wide variety of infectious pathogens.

12 Claims, No Drawings

5,547,677

ANTIMICROBIAL OIL-IN-WATER EMULSIONS

BACKGROUND OF THE INVENTION

The present invention relates to an antimicrobial lipid-containing oil-in-water emulsion which inactivates infectious pathogens upon contact.

Oil-in-water emulsions have discrete droplets of oil, called the "discominuous phase," dispersed in a "continuous phase" of water or an aqueous solvent. The discontinuous phase of the emulsion of the present invention binds to the biological membrane of a pathogen and subsequently solubilizes the membrane. The emulsion has microbicidal activity against a broad spectrum of bacteria and several yeasts.

It is known that if a water-iminiscible liquid phase, is mixed imo an aqueous phase by mechanical agitation, for example, by means of an ultra-disperser, the stability of the resulting oil-in-water dispersion most frequently requires the addition of an emulsifying agent, the molecules of which are adsorbed onto the surface of the oil droplets to form a kind of continuous membrane which prevents direct contact between two adjacent droplets. The drops of oil can further contain substances soluble in an organic medium, such as a sterol.

In addition to discrete oil droplets dispersed in an aqueous phase, oil-in-water emulsions can also contain other lipid structures, such as small lipid vesicles (i.e., lipid spheres which often consist of several substantially concentric lipid bilayers separated from each other by layers of aqueous phase), micelles (i.e., amphiphile molecules in small clusters of 50–200 molecules arranged so that the polar head groups face outward toward the aqueous phase and the apolar tails are sequestered inward away from the aqueous phase), or lamellar phases (lipid dispersions in which each particle consists of parallel amphiphile bilayers separated by thin films of water). TheSe lipid structures are formed as a result ofhydrophobic forces which drive apolar residues (i.e., long hydrocarbon chains) away from water.

The antimicrobial emulsion of the presem invemion consists primarily of positively charged droplets of a lipid-comaining oily discominuous phase dispersed in an aqueous cominuous phase, such as water. The discominuous phase comains an amphiphile selected from the group consisting of glycerol monooleate, glycerol trioleate, glycerol monolaurate, and glycerol dilaurate as the primary lipid and a cationic halogen-containing compound having a $C_{12}$–$C_{16}$ chain as a positive charge producing agent. The droplets can further contain a sterol, such as cholesterol or phytosterol. The droplets bind to negatively charged proteins contained in bacterial, viral, or fungal membranes, thereby disrupting the membrane structure and irradiating the pathogen.

Antimicrobial emulsions of the present invention are non-toxic and safe, for example, when swallowed, inhaled, or applied to the skin. This result is unexpected since many cationic halogen-containing compounds having a $C_{12}$–$C_{16}$ chain are extremely toxic if administered alone. For example, cetylpyridinium chloride (CPC), a preferred cationic halogen-containing compound of the invention, causes severe irritation and damage to tissues of the upper respiratory tract, mucous membranes and skin. However, when administered in the form of an emulsion of the invention, no such adverse effects occur. Furthermore, the emulsions of the invention are stable when heated or exposed to significant levels of acid and base.

The portals of entry of pathogenic bacteria, viruses or fungi are predominantly the skin and mucus membranes. The first step in any infection is attachment or colonization on skin or mucus membranes with subsequent invasion and dissemination of the infectious pathogen. Accordingly, an object of the present invention is to provide an antimicrobial emulsion which inactivates infectious pathogens on contact by disrupting their membrane structures.

SUMMARY OF THE INVENTION

The present invention provides a stable antimicrobial oil-in-water emulsion for inactivating infectious pathogens upon contact. The emulsion comprises positively charged droplets of a lipid-containing oily discontinuous phase dispersed in an aqueous phase. The oily discontinuous phase contains an amphiphile selected from the group consisting of glycerol monooleate (GMO), glycerol trioleate (GTO), glycerol monolaurate (GML), and glycerol dilaurate (GDL) as the primary lipid and a cationic halogen-containing compound having a $C_{12}$–$C_{16}$ chain as a positive charge producing agent. The discontinuous phase can further include at least one sterol, such as cholesterol or phytosterol.

The antimicrobial emulsions of the present invention can be used, for example, in pharmaceutical preparations (e.g., creams, solutions and suspensions) to inhibit the growth of a wide variety of infectious pathogens. Accordingly, the present invention also provides an antimicrobial preparation suitable for pharmaceutical administration made up of an antimicrobial emulsion of the invention and a pharmaceutically acceptable carrier. The preparation can be applied topically to skin surface areas, mucus membranes, or oral surfaces, for example, as a cream, gel, spray, or mouthwash. Alternatively, the preparation can be administered internally, for example, to inactivate pathogenic microorganisms. Accordingly, the present invention further provides a method for inhibiting the growth of an infectious pathogen by topical or oral administration of the antimicrobial emulsion of the invention.

DETAILED DESCRIPTION OF THE INVENTION

The present invention relates to a stable antimicrobial oil-in-water emulsion made of positively charged droplets of a lipid-containing oily discontinuous phase dispersed in an aqueous continuous phase. The oily discontinuous phase includes an amphiphile selected from the group consisting of glycerol monooleate (GMO), glycerol trioleate (GTO), glycerol monolaurate (GML), and glycerol dilaurate (GDL) as the primary lipid and a cationic halogen-containing compound having a $C_{12}$–$C_{16}$ chain as a positive charge producing agent.

The term "antimicrobial," as used herein, means having the ability to inactivate infectious pathogens. The term "inactivate", as used herein, includes but is not limited to killing or inhibiting growth. The term "infectious pathogen", as used herein, includes, but is not limited to fungi, viruses, bacteria, and parasites. The antimicrobial emulsion of the present invention inactivates a wide variety of infectious pathogens by binding to negatively charged proteins contained in the biological membrane of the pathogen, and disrupting the membrane structure. Accordingly, one aspect of the present invention provides an antimicrobial oil-inwater emulsion which is capable of binding to the membrane of a pathogen, such as a bacterium, a virus, or a fungus, and disrupting the membrane structure so that the pathogen is inactivated.

The oily discontinuous phase of the emulsion contains an amphiphile selected from the group consisting of GMO, GTO, GML, and GDL as the primary lipid. In a preferred embodiment of the invention, GMO is used as the primary lipid. The term "primary lipid", refers to the lipid which constitutes the greatest proportion by weight of any single lipid contained in the oily discontinuous phase.

The positive charge of the oily discontinuous phase is provided by a cationic halogen-containing compound having a $C_{12}$–$C_{16}$ chain. In a preferred embodiment, the cationic halogen-containing compound having a $C_{12}$–$C_{16}$ chain is selected from the group consisting of cetylpyridinium chloride (CPC), cetypridinium bromide (CPB), and cetyltrimethylammonium bromide (CTAB). Other cationic halogen-containing compounds having a $C_{12}$–$C_{16}$ chain which can be used as wall-forming materials in the lipid vesicles of the present invention include, for example, cetyltrimethylammonium chloride, cetyldimethylethylammonium bromide, cetylbenzyldimethylammonium chloride, cetyltributylphosphonium bromide, dodecyltrimethylammonium bromide, and tetradecyltrimethylammonium bromide.

The oily discontinuous phase can further contain at least one sterol selected from the group consisting of cholesterol, cholesterol derivatives, hydrocortisone, phytosterol, and mixtures thereof. The term "cholesterol derivatives," as used herein, includes but is not limited to sulfate and phosphate derivatives of cholesterol. Preferred sterols include phytosterols, such as soya sterol.

The term "emulsion," as used herein, includes both classic oil-in-water dispersions or droplets, as well as other lipid structures which can form as a result of hydrophobic forces which drive apolar residues (i.e., long hydrocarbon chains) away from water and drive polar head groups toward water, when a water immiscible oily phase is mixed with an aqueous phase. These other lipid structures include, but are not limited to, unilamellar, paucilamellar, and multilamellar lipid vesicles, micelles, and lamellar phases. These other lipid structures also contain an amphiphile selected from the group consisting of glycerol monooleate (GMO), glycerol trioleate (GTO), glycerol monolaurate (GML), and glycerol dilaurate (GDL) as the primary lipid and a hexadecyl cationic halogen-containing compound as a positive charge producing agent. These other lipid structures can also further include at least one sterol, preferably a phytosterol.

Accordingly, in another embodiment of the invention, at least a portion of the oily discontinuous phase may be in the form of lipid structures including, but not limited to, unilamellar, multilamellar, and paucilamellar lipid vesicles, micelles, and lamellar phases.

Oils useful in forming antimicrobial oil-in-water emulsions of the present invention include a broad spectrum of water-immiscible materials, such as soybean oil, avocado oil, squalene oil, squalane oil, sesame oil, olive oil, canola oil, corn oil, rapeseed oil, safflower oil, sunflower oil, fish oils, flavor oils, water insoluble vitamins, and mixtures thereof.

Antimicrobial oil-in-water emulsions of the present invention can be formed using classic emulsion forming techniques which are well known in the art. In brief, the lipid-oil phase is mixed with the aqueous phase under relatively high shear forces to obtain an oil-in-water emulsion containing oil droplets which are approximately 1 micron in diameter. More particularly, a positively charged lipid-containing oily discontinuous phase is formed by blending (a) an oil; (b) an amphiphile selected from the group consisting of GMO, GTO, GML, or GDL; and (c) a cationic halogencontaining compound having a $C_{12}$–$C_{16}$ chain, along with any other compatible amphiphiles or emulsifiers, such as Polysorbate 60, and any sterols or other lipophilic materials to be incorporated into the lipid-oil phase.

Once the lipid-oil phase is formed, it is heated and blended with an aqueous phase (e.g., water, saline, or any other aqueous solution which can hydrate the lipids) on a volume to volume basis ranging from about 1:4 to 1:2, preferably about 1:3 lipid-oil phase to aqueous phase. The lipid-oil and aqueous phases can be blended using, for example, a French Press, Novamix (IGI Inc., Buena N.J.) or syringe mixer, or, alternatively by hand using two syringes.

In one embodiment of the present invention, the antimicrobial oil-in-water emulsion is formed as follows: a lipid-oil phase containing approximately 21% by weight GMO, GTO, GML, or GDL, 0.8 to 0.9% by weight cationic halogen-containing compound having a $C_{12}$–$C_{16}$ chain, 67% by weight oil, 5% by weight Polysorbate 60 (Polyoxyethylene 20 sorbitan monostearate), and 6% by weight soya sterol is heated for approximately one hour at 86° C. The lipid-oil phase is then blended with an aqueous phase containing water at 65° C. using a 5 ml syringe machine on a volume to volume basis of 13 parts lipid-oil to 37 parts water.

Antimicrobial oil-in-water emulsions of the present invention provide the advantage of being stable in the presence of heat, acid, or base. For example, as shown below in Example 4, emulsions of the invention are not significantly altered or broken down when boiled or exposed to 1N Nitric acid or 1N sodium hydroxide. This stability makes the emulsions suitable for pharmaceutical administration, even internal administration.

Antimicrobial oil-in-water emulsions of the present invention can be used to inactivate a variety of infectious pathogens upon contact. As described in the examples below, microbes which are inactivated by the present invention include a wide variety of bacteria and fungi. For example, the presently disclosed emulsions can be used for oropharyngeal application, as a spray or mouthwash, to inactivate or prevent infection secondary to *Streptococcus pneumoniae*, Group A beta-hemolytic Streptococcus, *Haemophilus influenzae*, and *Neisseria meningitidis*. The presently disclosed emulsions can also be used for veneral application, as a cream, gel, or suppository to inactivate or prevent infection secondary to *Neisseria gonorrhoeae, Gardnerella vaginalis,* and Group B Streptococcus. The presently disclosed emulsions can also be used for dermatological application as a cream or gel to inactivate or prevent infection secondary to *Propionibacterium acnes, Staphylococcus aureus, Staphylococcus epidermidis, Propionibacterium acnes,* and Group B Streptococcus. In a preferred embodiment of the invention, antimicrobial emulsions of the present invention are used to prevent infection by gram positive bacteria.

Accordingly, the present invention also provides an antimicrobial preparation suitable for pharmaceutical administration consisting of the antimicrobial emulsion of the present invention and a pharmaceutically acceptable carrier. The term "pharmaceutically acceptable carrier," as used herein, refers to any physiologically compatible carrier for stabilizing emulsions of the present invention for pharmaceutical administrstion. Use of such media and agents for pharmaceutically active substances is well known in the art.

Except insofar as any conventional media or agent is incompatible with the emulsions of the present invention, use thereof in a pharmaceutical preparation is contemplated.

The present invention further provides methods for inhibiting the growth of an infectious pathogen by topical, or systemic administration of the antimicrobial emulsion of the present invention, preferably in the form of a pharmaceutical preparation. The term "topical," as used herein, includes application to mucous membranes, oral surfaces, skin, inner ear surfaces, or the surfaces of any bodily orifice, such as the vagina or rectum. The term "systemic", as used herein, includes any form of internal administration, including but not limited to, oral and intravenous administration.

The following examples will illustrate the efficacy of the invention.

EXAMPLES

Example 1

In this Example, lipid-containing oil-in-water emulsions having either GMO or GMS as the primary lipid and a charge producing agent were formed and characterized with regard to purity, pH and size of oil droplets.

Each emulsion was formed by first heating the lipid-oil phase for 1 hour at 86° followed by blending with water at 65° C. The lipid-oil phase and the water were blended using a 5 ml syringe machine on a volume/volume basis of 13 parts lipid-oil to 37 parts water.

Table 1 shows the amount of each chemical component used to form the lipidoil phase of emulsions having glycerol monooleate (GMO) as the primary lipid and cetylpyridinium chloride (CPC), cetylpyridinium bromide (CPB), or cetyltrimethylammonium bromide (CTAB) as positive charge producing agents.

TABLE 1

| Chemical Component | Weight |
| --- | --- |
| Glycerol monooleate | 3.43 grams (21% by weight) |
| Soya sterol (or cholesterol) | 0.96 grams (6% by weight) |
| Tween 60 | 0.84 grams (5% by weight) |
| Soybean oil | 11 grams (67% by weight) |
| Cetylpyridinium chloride ($C_{21}H_{38}NCl$) or | 130 milligrams (0.8% by weight |
| Cetylpyridinium bromide ($C_{21}H_{38}NBr$) or | 150 milligrams (0.9% by weight) |
| Cetyltrimethylammonium bromide ($C_{19}H_{38}NBr$) | 140 milligrams (0.85% by weight) |

Table 2 shows the amount of each chemical component used to form the lipidoil phase of an emulsion having glycerol monostearate (GMS) as the primary lipid and dimethyldioctadecylammonium bromide (DDDAB) as a positive charge producing agent.

TABLE 2

| Chemical Component | Weight |
| --- | --- |
| Glycerol monostearate | 3.43 grams |
| Soya sterol (or cholesterol) | 0.96 grams |
| Tween 60 | 0.84 grams |
| Soybean oil | 11 grams |
| Dimethyldioctadecyl ammonium bromide ($C_{38}H_{80}NBr$) | 240 milligrams |

Table 3 shows the amount of each chemical component used to form the lipidoil phase of an emulsion having glycerol monooleate (GMO) as the primary lipid and oleic acid as a negative charge producing agent.

TABLE 3

| Chemical Component | Weight |
| --- | --- |
| Glycerol monooleate | 3.43 grams |
| Soya sterol (or cholesterol) | 0.96 grams |
| Tween 60 | 0.84 grams |
| Soybean oil | 11 grams |
| Oleic acid | 108 milligrams |

Table 4 shows the amount of each chemical component used to form the lipidoil phase of an emulsion having glycerol monostearate (GMS) as the primary lipid and cetylpyridinium chloride (CPC) as a positive charge producing agent.

TABLE 4

| Chemical Component | Weight |
| --- | --- |
| Glycerol monostearate | 3.43 grams |
| Soya sterol (or cholesterol) | 0.96 grams |
| Tween 60 | 0.84 grams |
| Soybean oil | 11 grams |
| Cetylpridinium chloride ($C_{21}H_{38}NCl$) | 130 milligrams |

Table 5 shows the pH of the emulsions shown in Tables 1–4. Also shown is the size of the lipid-oil droplets of the emulsions measured on a Coulter LS 130 Laser sizing instrument equipped with a circulating waterbath.

TABLE 5

| Chemical Components of Emulsion | Charge | pH | Mean Coulter Size in Microns | Mean Coulter Range in Microns |
| --- | --- | --- | --- | --- |
| GMO/CPC | Positive | 3.72 | 1.049 | 0.720–1.401 |
| GMO/CPB | Positive | 4.31 | 0.891 | 0.680–1.124 |
| GMO/CTAB | Positive | 4.82 | 1.143 | 0.647–1.358 |
| GMS/DDDAB | Positive | 5.86 | 1.080 | 0.694–1.532 |
| GMO/Oleic acid | Negative | 4.45 | 1.078 | 0.738–1.448 |
| GMS/CPC | Positive | 3.72 | 1.047 | 0.677–1.497 |

Example 2

In this Example, the microbicidal activities of each of the emulsions described in Tables 1–4 were compared. For this purpose, the ability of each of the emulsions to kill Staphylococcus aureus type 8 was tested as follows:

Bacteria were inoculated into liquid media (Trypticase soy broth or Schaedler's broth) and incubated at 37° C. for 1–7 hours. An optical density at a wavelength of 650 nm and a quantitative culture were then performed on each broth culture. One milliliter of each bacterial broth was then mixed with one milliliter of emulsion for 10 or 30 minutes. Quantitative cultures were then performed in duplicate on each mixture. Plates containing bacteria were incubated at 37° C. for 18 hours and then counted.

The percentage of bacteria killed was then determined by the following equation.

$$\% \text{ kill} = \frac{(A - B)}{A} \times 100$$

A = The total number of bacteria innoculated
B = The total number counted after mixing with an emulsion Table 6 lists the percentages of Staphylococcus aureus type 8 killed by each emulsion or water after a 10 or 30 minute incubation with $2 \times 10^7$ bacteria.

TABLE 6

| Chemical Components of Preparation | Formula of Change | % Inactivate After a 10 Minute Incubation | % Inactivate After a 30 Minute Incubation |
|---|---|---|---|
| GMO/CPC | $C_{21}H_{38}NCl$ | 100 | 100 |
| GMO/CPB | $C_{21}H_{38}NCr$ | 100 | 100 |
| GMO/CTAB | $C_{19}H_{42}NBr$ | 99.99 | 99.99 |
| GMO/DDDAB | $C_{38}H_{80}NBr$ | 65 | 0 |
| GMO/Oleic acid | $C_{18}H_{34}0_2$ | 0 | 0 |
| GMS/CPC | $C_{21}H_{38}NCl$ | 65 | 0 |
| Water alone | $H_1O_2$ | 50 | 0 |

From Table 6 one can see that only the positively charged glycerol monooleate (GMO) emulsions inactivate *Staphylococcus aureus* type 8 while the positively charged glycerol monostearate (GMS/CPC) emulsion fails to inactivate. In addition, only the cationic compounds having a $C_{12}$–$C_{16}$ chain containing either chloride or bromide, i.e., CPC, CPB or CTAB and not the dioctadecyl cationic compound (DDDAB) were associated with significant microbicidal activity. The inactivateing of this bacterium is therefore more effective using GMO emulsions containing a chloride or bromide containing cationic compound having a $C_{12}$–$C_{16}$ chain.

Example 3

In this Example, the ability of the GMO/CPC emulsion formed in Example 1 to kill a variety of bacteria and yeast was tested. Table 7 lists the type/strain of a variety of gram positive bacteria tested. Table 8 lists the type/strain of a variety of gram negative bacteria tested. Table 9 lists two species of fungi (yeast) tested.

TABLE 7

| Bacteria | Type/Strain |
|---|---|
| Staphylococcus aureus | type 5/bacteremic isolate |
| Staphylococcus aureus | type 8/bacteremic isolate |
| Staphylococcus epidermidis | strain 977 |
| Group B Streptococcus | type III/neonatal sepsis isolate |
| Group A beta-hemolytic Streptococcus | type 1/ATCC#12344 |
| Listeria monocytogenes | type 2/ATCC#19112 |
| Streptococcus pneumoniae | type 5/ATCC#6305 |
| Streptococcus mutans | ATCC 25179 |
| Propionibacterium acnes | ATCC 6919 |
| Gardnerella vaginalis | ATCC 14018 |

TABLE 8

| Bacteria | Type/Stain |
|---|---|
| Escherichia coli | type 018:K1 |
| Escherichia coli | type 018:K- |
| Escherichia coli | type J5 (epimerase deficient) |
| Flavobacterium meningosepticum | Group A/ATCC#13253 |
| Haemophilus influenza | capsular type b/ATCC#33533 |
| Klebsiella pneumonia | type 012K+ |
| Pseudomonas aeruginosa | type FD-1 |
| Pseudomonas aeruginosa | MEP strain 2192 |
| Neisseria meningitidis | type B/ATCC 13090 |
| Neisseria gonorrhoeae | ATCC 9793 |

TABLE 9

| Yeast or Fungi | Type/Stain |
|---|---|
| Candida albicans | clinical blood isolate |
| Candida tropicalis | clinical blood isolate |

The assay described above in Example 2 was used to measure the microbicidal activity of the GMO/CPC emulsion, except for the following changes:

Yeast were innoculated into Sabouraud's broth and incubated at 30° C. for 6 hours, mixed with the GMO/CPC emulsion for 10 or 30 minutes, plated and incubated at 37 C for 18 hours befor counting.

*P. acnes* was grown in Schaedler's broth for 24 hours, mixed with emulsion for 10 or 30 minutes, plated on Trypticase soy agar plates with 5% sheep blood and incubated anaerobically for 72 hours prior to counting.

*G. vaginalis* was plated on Trypticase soy agar plates with 5% sheep blood and incubated in 5% $CO_2$ at 37° C. for 72 hours. Colonies were swabbed from plates and innoculated into Schaedler's broth at the density of a 0.5 McFarland standard. This broth/bacterial mixture was then incubated with the emulsion for 10 or 30 minutes and then plated on Trypticase soy agar plates with 5% sheep blood. Plates were incubated for 72 hours in 5% $CO_2$ at 37° C. before counting colonies.

Table 10 lists the percentage of gram positive bacteria listed in Table 7 killed after a 10 or 30 minute incubation of the GMO/CPC emulsion with $10^7$ bacteria. The listed bacteria can generally be categorized as follows: (a) those which colonize on the skin which include *Staphylococcus aureus* (type 8), *Staphylococcus aureus* (type 5), *Staphylococcus epidermidis* (strain 977), Group B Streptococcus (capsular type III), Group A Streptococcus (beta-hemolytic), and *Propionibacterium acnus;* (b) those which colonize in the oropharynx which include Group A Streptococcus (beta-hemolytic), *Streptococcus pneumoniae* (type 5), and *Streptococcus mutans;* and (c) those which colonize or infect the vagina which include *Gardnerella vaginalis* and Group B Streptococcus (capsular type III).

TABLE 10

| Bacteria | Innoculum (CFU)• | % Inactivate after a 10 Minute Incubation | % Inactivate after a 30 Minute Incubation |
|---|---|---|---|
| Staphylococcus aureus (type 8) | $2 \times 10^7$ | 99.99 | 99.99 |
| Staphylococcus aureus (type 5) | $9 \times 10^6$ | 100 | 99.99 |
| Staphylococcus epidermidis (strain 977) | $8 \times 10^5$ | 100 | 100 |
| Group B Streptococcus | $2.9 \times 10^7$ | 99.99 | 100 |

TABLE 10-continued

| Bacteria | Innoculum (CFU)* | % Inactivate after a 10 Minute Incubation | % Inactivate after a 30 Minute Incubation |
|---|---|---|---|
| (capsular type III) Group A Streptococcus (beta-hemolytic) | $3.3 \times 10^7$ | 99.99 | 99.99 |
| Listeria monocytogenes | $1.3 \times 10^8$ | 99.99 | 99.99 |
| Streptococcus pneumoniae (type 5) ATCC 6305) | $6.4 \times 10^7$ | 100 | 100 |
| Streptococcus mutans (ATCC 25179) | $6.5 \times 10^6$ | 96.2 | 96.8 |
| Propionibacterium acnus (ATCC 6919) | $1.2 \times 10^8$ | 100 | 100 |
| Gardnerella vaginalis (ATCC 14018) | $5.5 \times 10^7$ | 100 | 100 |

*CFU = colony forming units

Table 10 demonstrates that all gram positive bacteria which cause significant human clinical infections were exquisitely sensitive to the microbicidal action of the GMO/CPC emulsion.

Table 11 shows the percentage of gram negative bacteria listed in Table 8 killed after a 10 or 30 minute incubation of the GMO/CPC emulsion with $10^7$ bacteria. Included in the table are bacteria which colonize in the oropharynx, such as *Haemophilus influenzae* (capsular type b) and *Neisseria meningitidis* type b, as well as bacteria which colonize in the vagina, such as *Neisseria gonorrhoeae*.

TABLE 11

| Bacteria | Innoculum (CFU) | % Inactivate After a 10 Minute Incubation | % Inactivate After a 30 Minute Incubation |
|---|---|---|---|
| *Escherichia coli* type 018:K1 | $2.1 \times 10^7$ | 97.1 | 96.7 |
| *Escherichia coli* type 018:K- | $3.2 \times 10^7$ | 89.7 | 99.6 |
| *Escherichia coli* J5 (epimerase deficient) | $3 \times 10^7$ | 94 | 85 |
| *Flavobacterium meningosepticum* Group A | $2.1 \times 10^5$ | 0 | 47.6 |
| *Klebsiella pneumonia* type 012K+ | $5 \times 10^7$ | 98.3 | 99.9 |
| *Pseudomonas aeruginosa* type FD-1 | $3.8 \times 10^7$ | 99 | 99 |
| *Pseudomonas aeruginosa* MEP strain 2192 | $8 \times 10^6$ | 99.1 | 97.5 |
| *Haemophilus influenzae* capsular type b | $1 \times 10^7$ | 99.99 | 99.99 |
| *Neisseria meningitidis* type b (ATCC 13090) | $1.6 \times 10^8$ | 100 | 100 |
| *Neisseria gonorrhoeae* (ATCC 9793) | $1.2 \times 10^6$ | 100 | 100 |

Table 11 illustrates that at 30 minutes there is inactivateing of at least 85% of the innoculum of all gram negative bacteria tested except for *Flavobacterium meningosepticum*. The encapsulated type b *Haemophilus infiuenzae*, type b *Neisseria meningitidis*, and *Neisseria gonorrhoeae* bacteria, which have relatively rough LPS types compared to the other gram negative bacteria, are equisitely sensitive to the microbicidal activity of the GMO/CPC emulsion. Gram negative bacteria as a group are less sensitive to the GMO/CPC emulsion than gram positive bacteria.

Table 12 shows the percentage of the two Candida species listed in Table 9 killed after a 10 or 30 minute incubation of the GMO/CPC emulsion with $10^7$ yeast.

TABLE 12

| Yeast | Innoculum (CFU) | % Inactivate After a 10 Minute Incubation | % Inactivate After a 30 Minute Incubation |
|---|---|---|---|
| *Candida albicans* | $3.2 \times 10^5$ | 62.5 | 62.5 |
| *Candida tropicalis* | $5.4 \times 10^5$ | 100 | 100 |

Table 12 demonstrates that significant inactivateing of Candida species, occurs after only a 10–30 minute incubation with the GMO/CPC emulsion.

Example 4

In this Example, GMO emulsions containing different concentrations of CPC were tested for antimicrobicidal activity against *Staphylococcus aureus* type 8. Table 13 shows percentages of *Staphylococcus aureus* type 8 killed after a 10 or 30 minute incubation of the GMO emulsions with $10^7$ bacteria.

TABLE 13

| Chemical Components of Emulsion | Initial Innoculum of Staphyloccus Aureus Type 8 | % Inactivate After a 10 Minute Incubation | % Inactivate After a 30 Minute Incubation |
|---|---|---|---|
| GMO/CPC $C_{21}H_{38}NCl$ | 10,000,000 CFU [1.8 mg/ml emulsion] | 100 | 100 |
| GMO/CPC $C_{21}H_{38}NCl$ | 10,000 CFU [0.9 mg/ml emulsion] | 99.5 | 100 |
| GMO/CPC $C_{21}H_{38}NCl$ | 10,000,000 CFU [0.45 mg/ml emulsion] | 54 | 99.5 |
| GMO/CPC $C_{21}H_{38}NCl$ | 10,000 CFR [0.23 mg/ml emulsion] | 39 | 32 |
| GMO/CPC $C_{21}H_{38}NCl$ | 10,000 CFU [0.028 mg/ml emulsion] | 0 | 0 |
| GMO | 10,000,000 CFU | 0 | 0 |
| GMO/Oleic acid $C_{18}H_{34}O_2$ | 10,000,000 CFU | 0 | 0 |
| Water alone | 10,000,000 CFU | 10 | 0 |

Table 13 demonstrates that *Staphylococcus aureus* type 8 bacteria were sensitive to the microbicidal action of the GMO/CPC emulsion at CPC concentrations of greater than 0.23 mg/ml of emulsion.

Example 5

In this Example, the GMO/CPC emulsion formed in Example 1 was tested for stability in the presence of heat, acid and base. Table 14 shows the effect of boiling for one hour on breakdown or aggregation of the GMO/CPC emulsion. Table 15 shows the effect of mixing equal volumes of 1N Nitric acid and GMO/CPC emulsion for two hours on breakdown or aggregation of the GMO/CPC emulsion. Table 16 shows the effect of mixing equal volumes of 1N Sodium hydroxide and GMO/CPC emulsion for two hours on breakdown or aggregation of the GMO/CPC emulsion.

TABLE 14

| Chemical Components of Emulsion | Intervention | Mean Coulter Size in Microns | Mean Coulter Range in Microns |
|---|---|---|---|
| GMO/CPC | No boiling | 1.008 | 0.720–1.337 |
| GMO/CPC | Boiling 1 hour | 1.167 | 0.654–1.517 |

TABLE 15

| Chemical Components of Emulsion | Intervention | Mean Coulter Size in Microns | Mean Coulter Range in Microns |
|---|---|---|---|
| GMO/CPC | No acid treatment | 1.008 | 0.720–1.337 |
| GMO/CPC | 1N HNO$_3$ for 2 hours | 1.062 | 0.675–1.569 |

TABLE 16

| Chemical Components of Emulsion | Intervention | Mean Coulter Size in Microns | Mean Coulter Range in Microns |
|---|---|---|---|
| GMO/CPC | No base treatment | 1.008 | 0.720–1.337 |
| GMO/CPC | 1N NaOH for 2 hours | 0.804 | 0.658–0.969 |

Tables 14–16 show that: (a) boiling for 1 hour does not significantly alter the breakdown or size of the emulsion; (b) 1N Nitric acid exposure for 2 hours does not significantly alter the size or aggregate profile of the CMO/CPC emulsion; and (c) 1N Sodium hydroxide exposure for 2 hours causes a 20% decrease in the mean size of the emulsion without disrupting the emulsion or causing aggregation.

Conclusion

From the above-described Examples 1–4, it is evident that the antimicrobial oil-in-water emulsions of the present invention have significant microbicidal activity against a wide variety of bacteria and yeast, even at low concentrations of cationic halogen-containing compound, such as CPC. Furthermore, the emulsions of the invention are stable in the presence of heat, acid, and base, making them very suitable for pharmaceutical administration, whether topical, oral or systemic.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. An antimicrobial oil-in-water emulsion comprising positively charged droplets of a lipid-containing oily discontinuous phase dispersed in a continuous aqueous phase, the oily discontinuous phase consisting essentially of:
   a. an oil;
   b. glycerol monooleate as the primary lipid; and
   c. a cationic halogen-containing compound having a $C_{12}$–$C_{16}$ chain selected from the group consisting of cetylpyridinium chloride, cetylpyridinium bromide, cetyltrimethylammonium bromide, cetyltrimethylammonium chloride, cetyldimethylethylammonium bromide, cetylbenzyldimethylammonium chloride, cetyltributylphosphonium bromide, dodecyltrimethylammonium bromide, and tetradecyltrimethylammonium bromide.

2. An antimicrobial emulsion of claim 1, wherein the oil is selected from the group consisting of soybean oil, squalene oil, sesame oil, olive oil, canola oil, corn oil, rapeseed oil, safflower oil, sunflower oil, fish oils, avocado oil, water insoluble vitamins, and mixtures thereof.

3. The antimicrobial emulsion of claim 1, wherein at least a portion of the oily discontinuous phase is in the form of a lipid structure selected from the group consisting of unilamellar, multilamellar, and paucilamellar lipid vesicles, micelies, and lamellar phases.

4. An antimicrobial oil-in-water emulsion comprising positively charged droplets of a lipid-containing oily discontinuous phase dispersed in a continuous aqueous phase, the oily discontinuous phase consisting essentially of:
   a. an oil selected from the group consisting of soybean oil, squalene oil, sesame oil, olive oil, canola oil, corn oil, rapeseed oil, safflower oil, sunflower oil, fish oils, avocado oil, flavor oils, water insoluble vitamins, and mixtures thereof;
   b. glycerol monooleate as the primary lipid; and
   c. cetylpyridinium chloride.

5. An antimicrobial oil-in-water emulsion comprising positively charged droplets of a lipid-containing oily discontinuous phase dispersed in a continuous aqueous phase, the oily discontinuous phase consisting essentially of:
   a. an oil selected from the group consisting of soybean oil, squalene oil, sesame oil, olive oil, canola oil, corn oil, rapeseed oil, safflower oil, sunflower oil, fish oils, avocado oil, flavor oils, water insoluble vitamins, and mixtures thereof;
   b. glycerol monooleate as the primary lipid; and
   c. cetylpyridinium bromide.

6. An antimicrobial oil-in-water emulsion comprising positively charged droplets of a lipid-containing oily discontinuous phase dispersed in a continuous aqueous phase, the oily discontinuous phase consisting essentially of:
   a. an oil selected from the group consisting of soybean oil, squalene oil, sesame oil, olive oil, canola oil, corn oil, rapeseed oil, safflower oil, sunflower oil, fish oils, avocado oil, flavor oils, water insoluble vitamins, and mixtures thereof;
   b. glycerol monooleate as the primary lipid; and
   c. cetyltrimethylammonium bromide.

7. An antimicrobial oil-in-water emulsion comprising positively charged droplets of a lipid-containing oily discontinuous phase, dispersed in a continuous aqueous phase, wherein at least a portion of the oily discontinuous is in the form of a lipid structure selected from the group consisting of unilamellar, multilamellar, and paucilamellar lipid vesicles, micelies, and lamellar phases, and wherein the oily discontinuous phase consists essentially of a mixture of:
   a. an oil;
   b. glycerol monooleate as the primary lipid; and
   c. a cationic halogen-containing compound having a $C_{12}$–$C_{16}$ chain selected from the group consisting of cetylpyridinium chloride, cetylpyridinium bromide, cetyltrimethylammonium bromide, cetyltrimethylammonium chloride, cetyldimethylethylammonium bromide, cctylbenzyldimethylammonium chloride, cetyltributylphosphonium bromide, dodecyltrimethylammonium bromide, and tetradecyltrimethylammonium bromide.

8. The antimicrobial emulsion of claim 7, wherein the positively charged lipid structure is a lipid vesicle having glycerol monooleate as the primary structural component of the vesicle walls.

9. An antimicrobial preparation suitable for pharmaceutical administration comprising the antimicrobial emulsion of claim 1 and a pharmaceutically acceptable carrier.

10. An antimicrobial oil-in-water emulsion comprising positively charged droplets of a lipid-containing oily discontinuous phase dispersed in a continuous aqueous phase, the oily discontinuous phase consisting essentially of:
   a. an oil;
   b. glycerol monooleate as the primary lipid;
   c. a cationic halogen-containing compound having a $C_{12}$–$C_{16}$ chain selected from the group consisting of cetylpyridinium chloride, cetylpyridinium bromide, cetyltrimethylammonium bromide, cetyltrimethylammonium chloride, cetyldimethylethylammonium bromide, cetylbenzyldimethylammonium chloride, cetyltributylphosphonium bromide, dodecyltrimethylammonium bromide, and tetradecyltrimethylammonium bromide; and
   d. a sterol.

11. The antimicrobial oil-in-water emulsion of claim 10 wherein the sterol is selected from the group consisting of cholesterol, cholesterol derivatives, hydrocortisone, phytosterol, and mixtures thereof.

12. The antimicrobial oil-in-water emulsion of claim 10 wherein the oil is selected from the group consisting of soybean oil, squalene oil, sesame oil, olive oil, canola oil, corn oil, rapeseed oil, safflower oil, sunflower oil, fish oils, avocado oil, flavor oils, water insoluble vitamins, and mixtures thereof.

* * * * *

UNITED STATES PATENT AND TRADEMARK OFFICE
CERTIFICATE OF CORRECTION

PATENT NO. : 5,547,677
DATED : August 20, 1996
INVENTOR(S) : D. Craig Wright

Page 1 of 3

It is certified that error appears in the above-identified patent and that said Letters Patent is hereby corrected as shown below:

At column 1, line 8, replace "inactivatcs" with --inactivates--;

At column 1, line 11, replace "discominuous" with --discontinuous--;

At column 1, line 17, replace "water-iminiscible" with --water-immiscible--;

At column 1, line 39, replace "TheSe" with --These--;

At column 1, line 40, replace "ofhydrophobic" with --of hydrophobic--;

At column 1, line 42, replace "presem invemion" with --present invention--;

At column 1, lines 43-44, replace "lipid-comaining" with --lipid-containing--;

At column 1, line 44, replace "discominuous" with --discontinuous--;

At column 1, line 45, replace "discominuous" with --discontinuous--;

At column 1, line 46, replace "comains" with --contains--;

At column 2, lines 65-66, replace "oil-inwater" with --oil-in-water--;

At column 4, line 5, replace "sterols" with --sterols--;

At column 4, line 45, replace "Streptococcus" with --*Streptococcus*--;

At column 4, line 46, replace "*infiuenzae*" with --*influenzae*--;

At column 4, line 66, replace "administrstion" with --administration--;

At column 6, line 16, replace "lipidoil" with --lipid oil--;

At column 6, lines 56-57, replace "Staphylococcus aureus" with --*Staphylococcus aureus*--;

At column 6, line 59, replace "37°C." with --37°C--;

UNITED STATES PATENT AND TRADEMARK OFFICE
CERTIFICATE OF CORRECTION

PATENT NO. : 5,547,677
DATED : August 20, 1996
INVENTOR(S) : D. Craig Wright

It is certified that error appears in the above-identified patent and that said Letters Patent is hereby corrected as shown below:

At column 6, line 67, replace "37°C." with --37°C--;

At column 7, line 8, replace "Staphylococcus aureus" with --*Staphylococcus aureus*--;

At column 7, line 33, replace "inactivateing" with --inactivating--;

At column 7, lines 52-53, replace "beta-hemolytic Streptococcus" with --*beta-hemolytic Streptococcus*--;

At column 8, line 24, replace "37 C." with --37°C--;

At column 8, line 25, replace "befor" with --before--;

At column 8, line 32, replace "37°C." with --37°C--;

At column 8, line 37, replace "37°C." with --37°C--;

At column 8, line 45, replace "Group B Streptococcus" with --*Group B Streptococcus*--;

At column 8, line 46, replace "Group A Streptococcus" with --*Group A Streptococcus*--;

At column 8, line 48, replace "Group A Streptococcus" with --*Group A Streptococcus*--;

At column 8, line 52, replace "Group B Streptococcus" with --*Group B Streptococcus*--;

UNITED STATES PATENT AND TRADEMARK OFFICE
CERTIFICATE OF CORRECTION

PATENT NO. : 5,547,677
DATED : August 20, 1996
INVENTOR(S) : D. Craig Wright

It is certified that error appears in the above-identified patent and that said Letters Patent is hereby corrected as shown below:

At column 8, line 66, replace "Group B Streptococcus" with --*Group B Streptococcus*--;

At column 9, line 66, replace "inactivateing" with --inactivating--;

At column 13, line 1, replace "cctylbenzyldimethylammonium" with --cetylbenzyldimethylammonium--.

Signed and Sealed this

Tenth Day of February, 1998

Attest:

BRUCE LEHMAN

*Attesting Officer*   *Commissioner of Patents and Trademarks*